US008495707B2

(12) United States Patent
Miller

(10) Patent No.: US 8,495,707 B2
(45) Date of Patent: Jul. 23, 2013

(54) QUALITY ASSURED ANALYTICAL TESTING SYSTEM AND METHOD THEREOF

(75) Inventor: Steven Miller, Lucerne (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 679 days.

(21) Appl. No.: 12/543,610

(22) Filed: Aug. 19, 2009

(65) Prior Publication Data

US 2010/0050236 A1    Feb. 25, 2010

(30) Foreign Application Priority Data

Aug. 20, 2008   (EP) .................................... 08105083

(51) Int. Cl.
*H04L 29/06*        (2006.01)
(52) U.S. Cl.
USPC .................................. 726/3; 726/27; 434/262
(58) Field of Classification Search
USPC ............................................................. 726/3
See application file for complete search history.

(56) References Cited

U.S. PATENT DOCUMENTS

| | | | |
|---|---|---|---|
| 5,840,020 A * | 11/1998 | Heinonen et al. ............. | 600/309 |
| 6,382,882 B1 * | 5/2002 | Ouellette ....................... | 406/198 |
| 6,386,882 B1 * | 5/2002 | Linberg ......................... | 434/262 |
| 7,947,270 B2 * | 5/2011 | Franklin ....................... | 424/94.64 |
| 2002/0001794 A1 | 1/2002 | Melker et al. | |
| 2008/0184330 A1 | 7/2008 | Lal et al. | |
| 2010/0050236 A1 * | 2/2010 | Miller ............................ | 726/3 |

FOREIGN PATENT DOCUMENTS

| | | | |
|---|---|---|---|
| DE | 10058570 | * | 11/2000 |
| DE | 10058570 A1 | | 6/2002 |

OTHER PUBLICATIONS

English translation of DE10058570, Birkhoelzer, "Automatic qualification management system has training database, usage detector that records use of device,e.g. medical device, and passes pattern of use to qualification manager", Jun. 13, 2002 , downloaded from Espacenet.*
Program Management Method, Database WPI, Section Ch, Week 200377, Thomson Scientific, London, G.B.; Class B04, An 2003-821438: XP002546964 & JP 2003 256063 A (Sysmex Corp.) Sep. 10, 2003.
Point-of-Care Nurse Competency Traineer (NCT), Web-based training tool, Abbott Point of Care.
European Search Report, Appl. No. EP 09 16 7117.2-1245, Oct. 2, 2009.

\* cited by examiner

*Primary Examiner* — Jung Kim
*Assistant Examiner* — Ghodrat Jamshidi
(74) *Attorney, Agent, or Firm* — Dinsmore & Shohl LLP

(57) ABSTRACT

A system and method for quality assured analytical testing is disclosed. A user is prompted by the system questions which relate to an analytical test to be conducted or an analytical instrument to be employed. Input received by the system from the user is evaluated to determine to which degree the inputs are correct. The user is certified if the determined degree is above a preset threshold. Next, the user is prompted by the system for a user identification and if the user is a certified user, access is provided to a testing routine of the analytical instrument.

16 Claims, 4 Drawing Sheets a)

b)

c)

d)

e)

f)

g)

QUALITY ASSURED ANALYTICAL TESTING SYSTEM AND METHOD THEREOF

TECHNICAL FIELD

Embodiments of the present invention concern the field of analytical testing for diagnostic purposes, and particular to a quality assured analytical testing system and method thereof.

BACKGROUND

Diagnostic testing is valuable for providing doctors with clinical data for supporting their diagnoses and medical actions. One field of diagnostic testing is conducted with large analytical instruments in specialized laboratories. These instruments are operated by highly specialized operators which are very well educated for this purpose. Another field of diagnostic testing, which is primarily addressed by the present invention, is called bedside testing or point of care testing. This type of diagnostic testing is being done by nurses or medical staff primarily educated for patient care whom typically have not focused much on using diagnostic instruments. Quality assurance of this type of testing is therefore much harder to achieve, especially in view of the large number of persons involved. In the field of bedside testing or point of care testing the testing is done on patients by typically nurses, medical staff or doctors which are collectively called "users" herein.

According to the prior art, there is very little quality assurance of analytical testing which is mostly based on self-training by users or by an administrator/supervisor who trains users in person so that the quality of diagnostics tests they perform will be sufficient and reliable. Certain testing instruments, such as e.g. the Accu-Check Inform system from Roche Diagnostics, allow control over who is allowed to do testing. For this purpose a list of users is stored in such an instrument and only these users can log in and do testing. However, registering of such users to the list is being done by a supervisor based on his personal decision.

SUMMARY OF THE INVENTION

It is against the above background, that embodiments of the present invention allow a much tighter and more reliable control of instrument usage so that only well educated users with proven knowledge are allowed to do testing with the analytical instrument. For this purpose exams are set up which need to be taken by users who want to be certified for doing testing. Checking the answers of examined users in response to questions which concern the particular analytical instrument and/or an analytical test to be performed helps to assure that all users of an analytical instrument have a sufficient knowledge about the instrument and related testing procedures. Wrong or unreliable test data can so be avoided to a greater extent. Performing the exam with a computerized examination tool (e.g., desktop or web-based), ensures that all important topics are checked which a human trainer, on a case by case training of users, could forget. Further it can be ensured that the examination conditions are the same for all examined users so that personal preferences of the trainer are excluded. As earlier mentioned, a large number of people are involved in bedside testing and so individual training of these persons by a supervisor/trainer would require high efforts which can be reduced by the present invention.

In one embodiment, a system for quality assured analytical testing is disclosed. The system comprises an analytical instrument which has an input section for determining an actual user and further has as a testing section which runs a testing routine. The system further comprises an examination module which is programmed to conduct an exam for a potential user during which it prompts questions to the user which relate to the analytical instrument and/or a diagnostic test to be conducted therewith and receives answers from the user to the questions and evaluates the answers. The examination module further determines if the user has passed the exam and if so, transmits a user certificate to the analytical instrument. The analytical instrument is programmed to control access to a testing routine by the user and only provides access to it if a user certificate for the actual user is available.

In another embodiment, a method for quality assured analytical testing is disclosed. The method comprises prompting questions to a user which relate to analytical tests to be conducted or an analytical instrument to be employed; receiving inputs from the user to those questions; and evaluating the inputs and determining to which degree the inputs are correct. If the determined degree of correct answers is above a threshold the user will be certified. In advance of analytical testing the user is prompted to input a user identification and it is being determined by the instrument if the user is a certified user. In the case that the user is a certified user, access to a testing routine of the analytical instrument is provided.

Further advantageous embodiments and combinations of features of the invention result from the following detailed description and the totality of the patent claims.

BRIEF DESCRIPTION OF THE DRAWINGS

In the figures, identical parts are in principle provided with the same reference symbols. In the drawings used to explain the exemplary embodiment.

DETAILED DESCRIPTION

Figure 1:
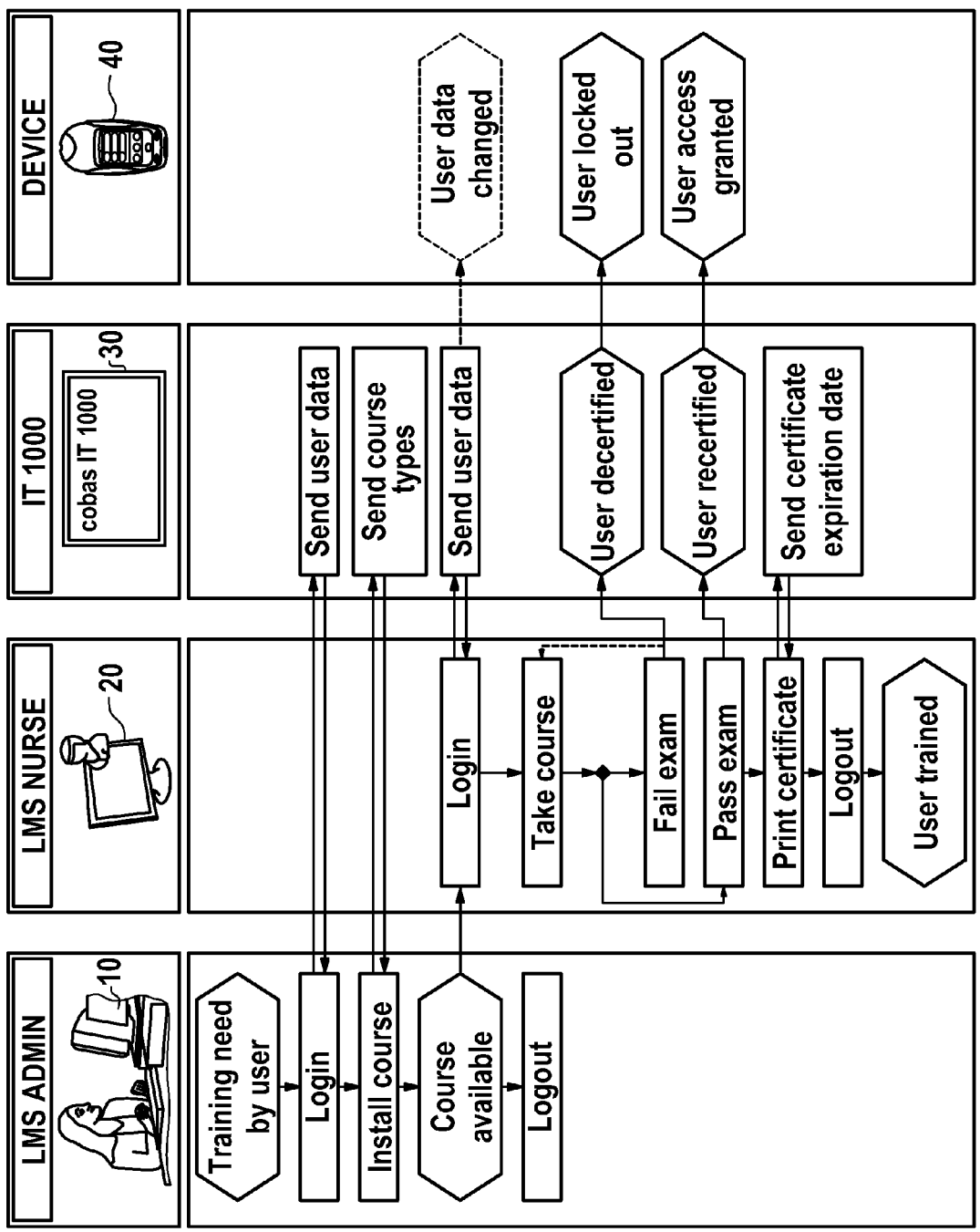
FIG. 1 depicts a workflow and setup for quality assured analytical testing.

The figures describe various embodiments of the present invention by examples and are in no way intended to limit the scope of the present invention.

Analytical testing according to the embodiments of the present invention means that a patient sample is reacted with reagents to perform a chemical or biochemical reaction resulting in a detectable change which allows to detect or quantify an analyte. Typical patient samples are blood, salvia, tissue, interstitial fluid, spinal fluid and the like. Often such patient samples are treated before analytical testing is done. Blood sampled from a patient is e.g. centrifuged to obtain serum or treated with anti-coagulants to obtain plasma. The term "patient sample" is meant to cover treated original patient samples as well.

According to the embodiments of the present invention, the patient sample is removed from the patient prior to analytical testing by e.g. a vacutainer for sampling blood (i.e., vacuum blood collection tube), a syringe or by a finger prick and taking up the blood with a test element. This means that analytical testing is performed extra corporal. Analytical testing has the goal to determine the presence and/or concentration of an analyte in a patient sample. "Analyte" is a general term for substances for which information about presence and/or concentration is intended. Exemplary analytes are e.g.

glucose, coagulation parameters, endogenous proteins (e.g. proteins released from the heart muscle), metabolites, nucleic acids and so on.

Reagents for analytical testing are well known in the art. Typical reagents e.g. comprise enzymes reacting with an analyte to obtain detectable products or e.g. antibodies which specifically bind to an analyte (i.e. an immunological reaction) for indicating presence and/or concentration of the analyte.

According to the embodiments of the present invention, analytical testing is preferably performed with test elements which contain reagents and which are discarded after analytical testing. Such test elements are e.g. the well known test strips for testing blood glucose or test strips for measuring coagulation parameters. There are, however, also test elements in the form of cartridges for e.g. immunological testing.

An analytical instrument according to an embodiment of the present invention preferably is a bedside testing instrument as e.g. a blood glucose or coagulation testing meter. An analytical instrument according to another embodiment of the present invention may further be an analytical instrument as used in bedside testing or critical care as e.g. a blood gas analyzer. These analytical instruments are typically operated by medical staff who are not primarily employed to set up and administrate analytical instruments.

The analytical instruments determine the presence and/or concentration of analytes by measuring detectable changes due to a reaction of analytes with reagents. Suitable detection methods are e.g. optical (e.g. absorption, remission, fluorescence) or electrochemical (e.g. amperometric, conductometric, coulometric, etc).

The analytical instruments according to other embodiments of the present invention have an integrated or co-located input section for receiving user inputs as user ID's (=identifications), passwords and information related to analytical testing. The input section further may receive information regarding patients on which testing is conducted (e.g. patient ID, age, sex). The input section typically comprises a display and input keys or a keyboard. If a touch screen is employed further input keys may be obsolete. The input section at least allows input of information which allows to identify the actual user. In this respect the input section may also be a barcode reader, a fingerprint reader, an ID card reader or the like to read an identification means in the possession of the user.

The instrument further comprises a microprocessor programmed to perform a testing routine for conducting an analytical test. The instrument checks if the current user is a certified user and if so, allows him to conduct the testing routine. This can be done by selecting the testing routine on the instrument by e.g. pressing a key of the instrument (e.g. a region on a touch screen). The instrument then conducts analysis by e.g. treating an electrochemical test strip with a voltage profile and reading a current profile or by illuminating an optical strip and recording reflected light. Further interactions by the user may be required as e.g. input of calibration data, insertion/change of test elements, input of comments.

Further types of analysis as for example in the field of blood gas testing are well known and therefore not described in more detail here.

A system according to an embodiment of the present invention further comprises an examination module which is programmed to conduct an exam. The examination module may be a programmed computer and is interactive in the sense that it prompts questions to a user and receives answers. The examination module may further reside on a programmed analytical instrument, the internet or may be even distributed over certain physical locations as a server of an instrument management system and a client computer. The questions are typically set up or selected by an administrator and replace those questions which he otherwise would ask a user in person to check if the user is able to employ the analytical instrument or to perform a diagnostic test without systematic errors.

According to one embodiment of the present invention it is also possible to set up standard exams by specialists and to provide the LMS administrator with either complete exams or modules from which he can choose. Such specialists may be e.g. employees of the manufacturer of analytical instruments who know the details of the instruments and also legal/regulatory requirements for clinical testing. Certain embodiments of the present invention therefore provides an option for hospitals and labs to employ administrators who focus on administration but do not need to be experts in analytical testing or knowing the analytical instruments in very detail.

Questions posed by the examination module may concern the pre-phase of analytical testing which involves a handling of the instrument or the preparation of the patient (e.g. cleaning a lancing site on the patient skin where a blood sample is to be taken). The questions may further relate to the testing procedure as such, e.g. how a test strip or a module of a blood gas analyzer is fed with a blood sample and how the instrument is operated to do the analysis. Further the questions may concern the phase after analysis which inter alia comprises the storage or transfer of analytical data and the discharge of analytical items (e.g. test strips or lancets) without contamination. Questions can also concern clinical knowledge, materials (test strips etc.) and maintenance.

The examination module receives answers from the user preferably by multiple choice, which means that a number of predefined answers are displayed to the user and the user can select one or more of these answers to be correct. Receiving answers alternatively or in addition may also involve the input of text by the user or a drag and drop exam where the user needs to drop certain predefined terms on the respective parts of an analytical instrument which are shown on a screen. The input of answers by the user may also be conducted by speech.

The examination module determines if the user has passed the exam. This may be conducted by a plain comparison of the user answers with predefined correct answers and counting the number of correct answers versus wrong answers. Such a plain evaluation of the answers may be replaced or accompanied by more sophisticated evaluations as described in more detail for FIG. 1.

The administrator may have the choice to define the type of evaluation and setting the thresholds when a user can be regarded to be experienced enough for using the particular analytical instrument and for conducting the respective analytical test. Preferably the computer is programmed by a software which supports the administrator in setting up the questions as well as in setting up the passing criteria of the exam. In the case of an exam which was set up/provided by a specialist or instrument manufacturer it preferably already comprises the passing criteria or at least a scheme which supports the administrator to define the passing criteria.

The examination module decides based on the user answers and the predefined passing criteria if the user has passed the exam. If the user has passed, the examination module transmits a user certificate to the analytical instrument. This can be a direct transfer to the instrument(s) or it can happen via intermediary devices, e.g. a server running an Instrument Management System. Passing on the certificate to the instrument is not limited to a push-service as described before but also may be a pull-service where the instrument pulls the certificate.

A user certificate is an information or a physical embodiment thereof which allows the analytical instrument to decide if the actual user has passed an exam so that he is allowed to do testing. In particular, a user certificate according to the present invention is not restricted to embodiments which are titled "certificate" or physical embodiments having a related title. In a simple case, a user certificate according to the present invention is provided by an entry of a user in a list of certified users. In this case the instrument checks if the user who logs in is on the list of certified users. If a user logs in who is not on the certified user list he will not be granted access to the testing section of the analytical instrument. The entry into the user list may be a user ID, a representation of a user and/or a password employed by the user. Further, the entry may comprise a date of issuance of the certificate or a date of expiry. Based on this, the analytical instrument can check if the certificate for the actual user is still valid at the time of log-on. Preferably, and in one embodiment, the user certificate is stored in the analytical instrument. It is, however, also possible in other embodiments that the analytical instrument retrieves the information if the user is a certified user from a connected device, e.g. a server. Further details and embodiments disclosing how such a certificate transfer can be accomplished and which data/information are transmitted is described in more detail for the embodiment of FIG. 1 discussed hereafter in a later section.

The analytical instrument has a microprocessor which is programmed to check if a user certificate for the actual user is available. As mentioned before, the analytical instrument has an input section for determining the actual user. Based on this input and the user certificates stored in the instrument it can be determined if the user is certified to use the particular instrument and/or the analytical test he intends to conduct. This check is described in more detail for the embodiment of FIG. 1. It should, however, be noted that the check of certificate may also involve checking which test the user actually wants to perform and also a check of the current date. Checking the date is important if the certificates are only valid for a certain timeframe, what often is the case or may be even required by law. Checking the test intended by the user allows to check if the user is certified to conduct this particular analytical test. This means the certificates according to the present invention may be specific for the type of the instrument as well as specific for the analytical tests. Accordingly the user may be certified for specific tests only and so the instrument would allow him to perform the respective tests while excluding him from other analytical tests.

Embodiments of the present invention further concern a method for quality assured analytical testing. During this method the user is prompted with questions which relate to analytical test to be conducted or an analytical instrument to be employed. As mentioned before, this prompting is initiated by an examination program. The prompting typically appears on a screen of a workstation or other device which the user uses to run the examination program. The user typically also makes his inputs to enter the answers at the same workstation or device. The inputs rendered by the user for answering the questions are evaluated to determine to which degree the inputs are correct. Particulars of this evaluation have already been described before or will be described in the context of FIG. 1. In the case that the degree of correct inputs is above a preset threshold, the user is certified to be a certified user. When the user intends to do an analytical test with an instrument he needs to input his user identification. Based on the user identification it is determined if the user is a certified user, which means that a certificate for this particular user is available. In the case that the instrument has determined the user to be a certified user, the instrument provides access to a testing routine to allow the user to perform analytical testing. Reference is now made to FIG. 1.

FIG. 1 shows the principal workflow underlining a system according to an embodiment of the present invention. FIG. 1 depicts four columns which represent four different system components and locations for conducting the respective steps. The system components in one embodiment comprise a local workstation 10, a terminal 20, an Instrument Management System (IMS) 30, and a device 40. The left most column (herein also referred to as the first column) shows actions taken by a supervisor referred herein as a Learning Management System (LMS) administrator on the local workstation 10. In the case that the LMS administrator decides that a training of users of a diagnostic instrument is necessary, the LMS administrator logs in to an Instrument Management System (IMS) 30 by e.g. using the local workstation 10. The IMS 30 comprises a computer which is directly or indirectly connected to analytical instruments to be managed such as e.g., device 40. The computer of the IMS 30 in one preferred embodiment is a server but in other embodiments other types of microprocessor based devices are also possible as well as being implemented by the local workstation 10. The computer of the IMS 30 is programmed by a software which allows management of the connected analytical instruments. Such management comprises the retrieval of analytical data from the instruments and may also comprise the download of program data or content data to the instruments. Program data would program the instruments to operate in a different way, e.g. a new input screen or a changed voltage profile for performing testing with electrochemical test strips. Content data are e.g. changed thresholds for warning messages or calibration data for calibrating the instruments.

The LMS administrator may retrieve user data from the IMS 30 for reviewing active users or changes in a user list and may create additional user accounts within the system. Further the LMS administrator may enter into the IMS data of further users who will do testing with analytical instruments in the future. The LMS administrator then installs an exam which means he/she sets up an examination for users who want to be certified or installs an exam provided by an expert, e.g. a manufacturer of the analytical instruments. By a suitable software running on the local workstation 10 the LMS administrator may set up an examination from scratch or he/she may retrieve a course already available on the instrument management system and modify it. The LMS administrator may further set up different exams (exam types) for different groups of users and/or different exam types for different instruments or even for different analytical tests. There may be for example different courses for nurses and medical staff who do plain diagnostic testing and more advanced courses for local administrators who administrate the analytical instruments. This local type of administration may involve the set up of instrument screens, activation of certain testing routines, changes of user profiles and quality control of the instruments.

After setting up a course, the LMS administrator may spread the information that a new course is available. This information can be spread verbally, by information (e.g. pop up) on a user terminal or the information can be transmitted to the analytical devices to be shown on the screen. Further it is possible that a user of a diagnostic instrument simply recognizes the need for new examination due to the fact that he/she cannot log on to the analytical instrument or run a testing routine because he/she is no longer certified.

The next column in FIG. 1, herein referred to as the second column, is titled "LMS nurse". The second column schematically shows the terminal 20 for users of the diagnostic instruments. When a user (in most cases a nurse) wants to perform an exam for becoming certified, the user logs on to the IMS 30 which, for example, can be done via an intranet or web-based tool via the terminal 20. The terminal 20 can be e.g. a client computer. The user then can choose an exam dedicated to the instruments or analytical test that the user wants to perform in the future. When the user has chosen an exam, certain questions as defined by the LMS administrator are prompted and the user can input his answers via the terminal 20. Preferably, in one embodiment the answers are given by multiple choice selections, but answers by typing or speech input may also be possible in other embodiments.

The answers given by the actual user are compared to correct answers as defined by the LMS administrator or by the author of the exam. If the degree of correct answers is above a threshold the user will be registered as a certified user by the IMS 30. The degree of correct answers may be determined by a plain number of correct and wrong answers or the single questions can be rated so that for example questions relating to the avoidance of analytical mistakes are more important than e.g. to know how to change the battery. It may also be provided that a wrong answer to a very important question may lead to failing the exam if making the same mistake in practice would lead to analytical errors. If the user fails the exam he may be de-certified instead of certified by the IMS 30.

Certification can be handled in various ways. In the most simple case, the system registers the user ID and so this user becomes "known" to the system and the user can log on to the instrument or run a testing routine later on. This would mean that the instrument, e.g., device 40, only allows testing for users which input a user ID known to the instrument. The de-certification of a user in this context would mean to delete him from the list of certified users.

Alternatively, the system may use a flag connected to a user ID to indicate if a certain user is a certified or an non-certified user. In the latter case the instrument, e.g., device 40, checks for a user who logs on to the instrument if the flag has a "certified" status. Instead of a plain flag it is also possible to employ a data field which indicates the date on which the respective user has passed the exam or alternatively a future date up to which the user is certified. Both options allow an improved quality control because the LMS administrator may determine a time frame for which a once issued certificate is valid. In the first case the LMS administrator may set a time frame of e.g. one year and after passing this year the certificate for the respective user will be automatically withdrawn or the instrument, e.g., device 40, may recognize that the certificate has expired. If the LMS administrator sets a future date e.g. one year after passing the exam, the instrument, e.g., device 40, compares this date with the actual date and if the date of certificate expiry lies in the past the instrument may deny access to its testing routine.

As further shown in FIG. 1, a user may be able to print his/her certificate for documentation. From a regulatory standpoint it is of high importance in hospitals to document that medical care people are well educated. This can be very well supported by the system according to the present invention.

The third column in FIG. 1 schematically shows a screen of the Instrument Management System (IMS) 30. The core of such an IMS is typically a server on which the IMS program runs. In the depicted case, the cobas IT 1000 software provided by Roche Diagnostics is employed. The IMS 30 (e.g. server) is connected to analytical instruments, e.g., device 40, in a way which will be described later on. Another connection of the IMS 30 that may be provided is to a so called hospital information system (HIS) which holds data of patients, doctors, nurses and so on. The IMS 30 primarily holds the data of performed analytical tests, the instruments and data to be used for test evaluation as e.g. calibration data. In one embodiment, the IMS 30 (e.g., server) can be accessed by the LMS administrator via the workstation 10. Users (in the present case a LMS Nurse as indicated in the second column) who wants to become certified, logs on to the IMS 30 (e.g., server) with the workstation terminal 20 which is for example installed in a nurse office. According to the present invention the IMS 30 (e.g., server) may further hold the exam. Alternatively, the exam may be stored on a different computer or server which the IMS 30 may access.

For conducting further embodiments of the present invention, the IMS 30 has or receives the information providing which users are certified. The IMS 30 then transmits this information to the connected analytical instruments, e.g. device 40, so that the instruments later on can control access. As mentioned earlier instead of the plain certification for specific patients or a list of certified patients the IMS 30 may establish or receive the expiration date or alternatively the term of validity of a certificate.

The right most column in FIG. 1, herein referred to as the fourth column, shows an analytical instrument or device 40 for diagnostic testing. In one embodiment, a suitable analytical instrument or device 40 is an Accu-Chek Inform blood glucose meter which is available from Roche Diagnostics. Details of this instrument will be provided later on. In other embodiments, other blood glucose testing devices may also be used with the embodiments of the present invention.

The analytical instrument or device 40 receives information from the IMS 30 according to certified users. This may be a push service where the server hosting the IMS 30 e.g. sends a list of certified users to the analytical instrument or it may be a pull service where the analytical instrument asks the server for such a list of certified users. Alternatively the analytical instrument or device 40 may request from the IMS 30 the status of certification for an actual user who tries to log in to the analytical instrument or device 40. For this purpose the analytical instrument or device 40 has an input section in to which the user inputs a user identification. If the user is a certified user and his certificate is valid the analytical instrument allows access to its analytical routine. The procedure of user input and analytical testing will be described later on in more detail.

Figure 2:
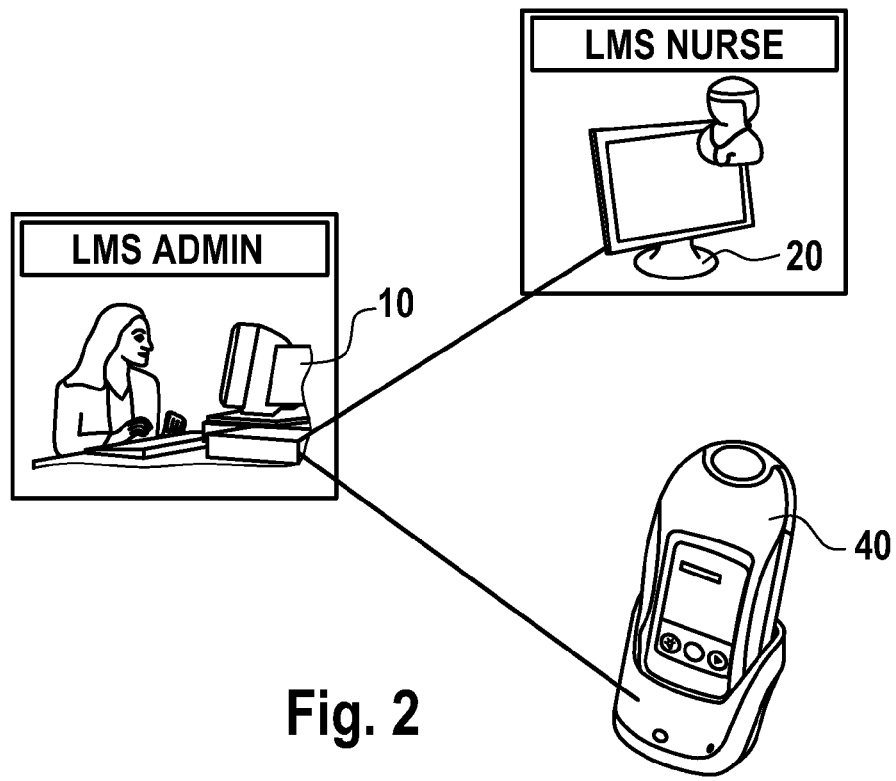
FIGS. 2 and 3 each depict alternative system setups.

FIG. 2 shows a different set up according to another embodiment of the present invention. It can be seen that certain embodiments of the present invention can be practiced without the need of an Instrument Management System, e.g. IMS 30. According to the set-up of FIG. 2 the LMS administrator sets up an examination on the local workstation 10 and makes it available for users. A user may log in on the workstation terminal 20 and logs on to the workstation 10 of the LMS administrator to conduct the examination. When the user passed the exam, the user will be certified and the workstation 10 of the LMS administrator transmits the user certificate to the analytical instrument or device 40. Details in which way certifications are transmitted to the analytical instrument or device 40 have already been described in respect of FIG. 1 and can be applied to the set-up of FIG. 2 and in an analogous manner.

Figure 3:
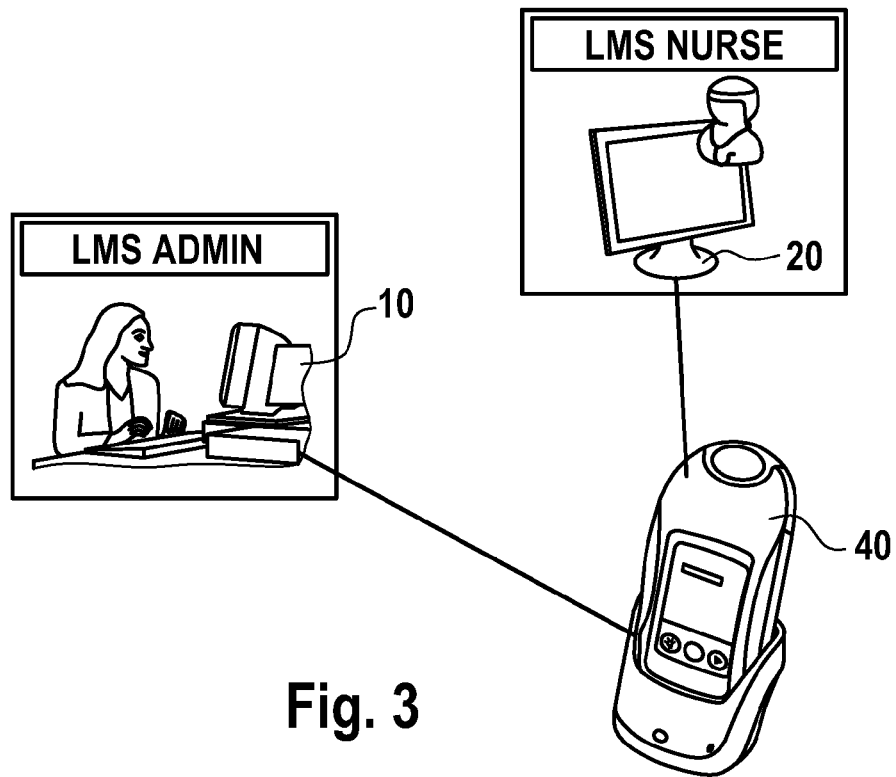

FIG. 3 depicts an instrument centric embodiment of the present invention. The LMS administrator creates an examination on workstation 10 and stores the examination in the analytical instrument or device 40. The user may access the instrument from the workstation terminal 20 and conducts the examination as provided by the analytical instrument or device 40. Based on the examination result, the analytical instrument or device 40 allows access for the user to the analytical testing section of the analytical instrument or device. Alternatively to using a workstation, the exam may be conducted directly on the analytical instrument or device 40. A number of instruments in intensive care units, e.g. blood gas analyzers have a screen large enough to conduct an exam but even on the smaller screen of a handheld analytical meter and the limited input keys of such an instrument simple exams are possible.

Figure 4:
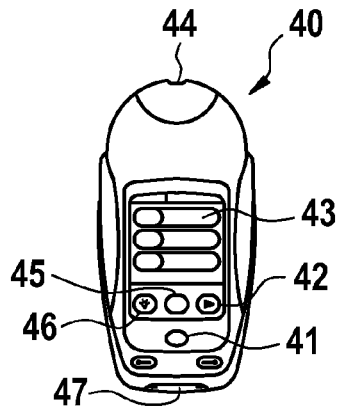
FIGS. 4a-g depict an analytical device according to an embodiment of the present invention.
Figure 4:
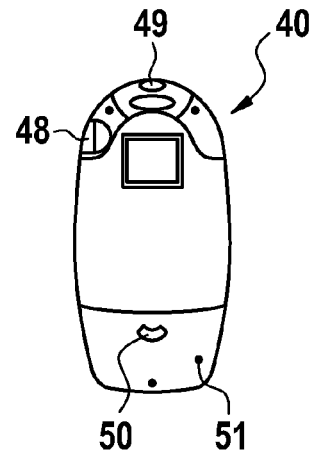
Figure 4:
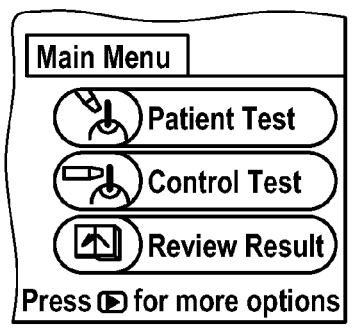
Figure 4:
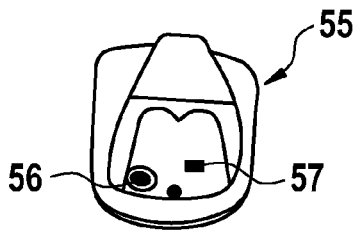
Figure 4:
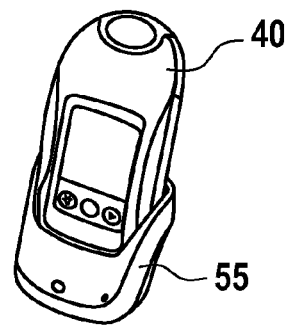
Figure 4:
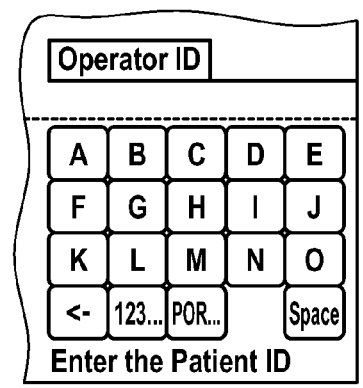
Figure 4:
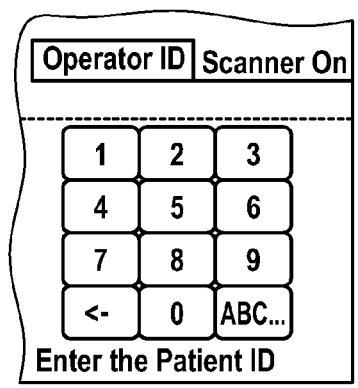

FIG. 4 depicts some more details of the analytical instrument or device 40, such as e.g., a blood glucose meter, as employed in the foregoing examples. FIG. 4a shows the front side of the instrument while FIG. 4b shows the back side. The instrument has a centrally located on/of-button 41 and a so called forward arrow button 42 for moving from one screen to another. A central feature of the instrument is the touch screen 43 which operates as display and further allows multiple user inputs. The depicted instrument employs disposable diagnostics tests strips. The instrument has a test strip slot 44 to receive the disposable strips. In another central position the instrument has a menu button 45 for going to the main menu screen at any time. Another feature of this instrument which makes it specifically useful for the hospital environment is the backlight button 46 which allows to turn on the backlight for the display. At the bottom side the analytical instrument has a connector 47 for connecting it to a base unit which will be described later on.

FIG. 4b shows the back side of the instrument which has a code chip slot 48 for receiving a code chip. The code chip allows to calibrate the analytical instrument or device 40 in respect of the lot of test strips actually employed. At the top side the instrument has a scanner 49 which emits a laser beam for barcode scanning. With this scanner 49 the instrument can read patient information from e.g. a wristband of a patient so that no manual input of a patient identification is necessary. Further, a barcode of the instrument user may be read to identify the actual user (the barcode scanner therefore may be also regarded as an input section according to the present invention). It is further possible that the user may scan a printed certificate certifying that he has passed the exam. This print-out may e.g. comprise a barcode which indicates the user, the passed exam and the expiry of the certificate. For logging in to the analytical section of the instrument the user may just scan the barcode on the printed exam and by that log in to the analytical section of the instrument. In a preferred embodiment, the user further needs to input a user ID and/or a password, so that it can be prevented that another person just takes a printout and uses it for identification.

FIG. 4b further depicts a battery compartment 50 as well as a reset button 51.

FIG. 4c shows an enlarged view of the instrument touch screen 43. As can be seen the main menu allows to choose between conducting a patient test, conduction a control test or reviewing testing results. By pressing onto the "patient test" region of the touch screen 43 the user selects to conduct a patient test and will only be granted access if he/she is a certified user. Alternatively, the analytical instrument or device 40 may ask the user at this point for his/her user identification for checking if the current user is a certified user.

FIG. 4d shows the base unit 55 which is also called cradle. The base unit 55 has a data port 56 and a power connector 57. When the analytical instrument or device 40 is placed onto the base unit 55 as shown in FIG. 4e the instrument connects to the data port as well as to the power connector for charging the instrument. The base unit 55 may be connected via a cable or a radio frequency transmitter to the Instrument Management System 30 in the embodiment of FIG. 1, to the workstation 10 of the administrator in the case of the embodiment of FIG. 2, or to an administrator workstation 10 and a user workstation terminal 20 in the case of the embodiment of FIG. 3. As well known in the art, this connection does not necessarily need to be a direct connection but can be also established via servers and a network (e.g. a local area network, a wide area network or the internet).

FIGS. 4f and g further show input screens of the analytical instrument or device 40. As can be seen the touch screen 43 allows input of numbers as well as alphanumeric characters. This input can be used to enter patient IDs, operator IDs, remarks, messages and further information.

Figure 5:
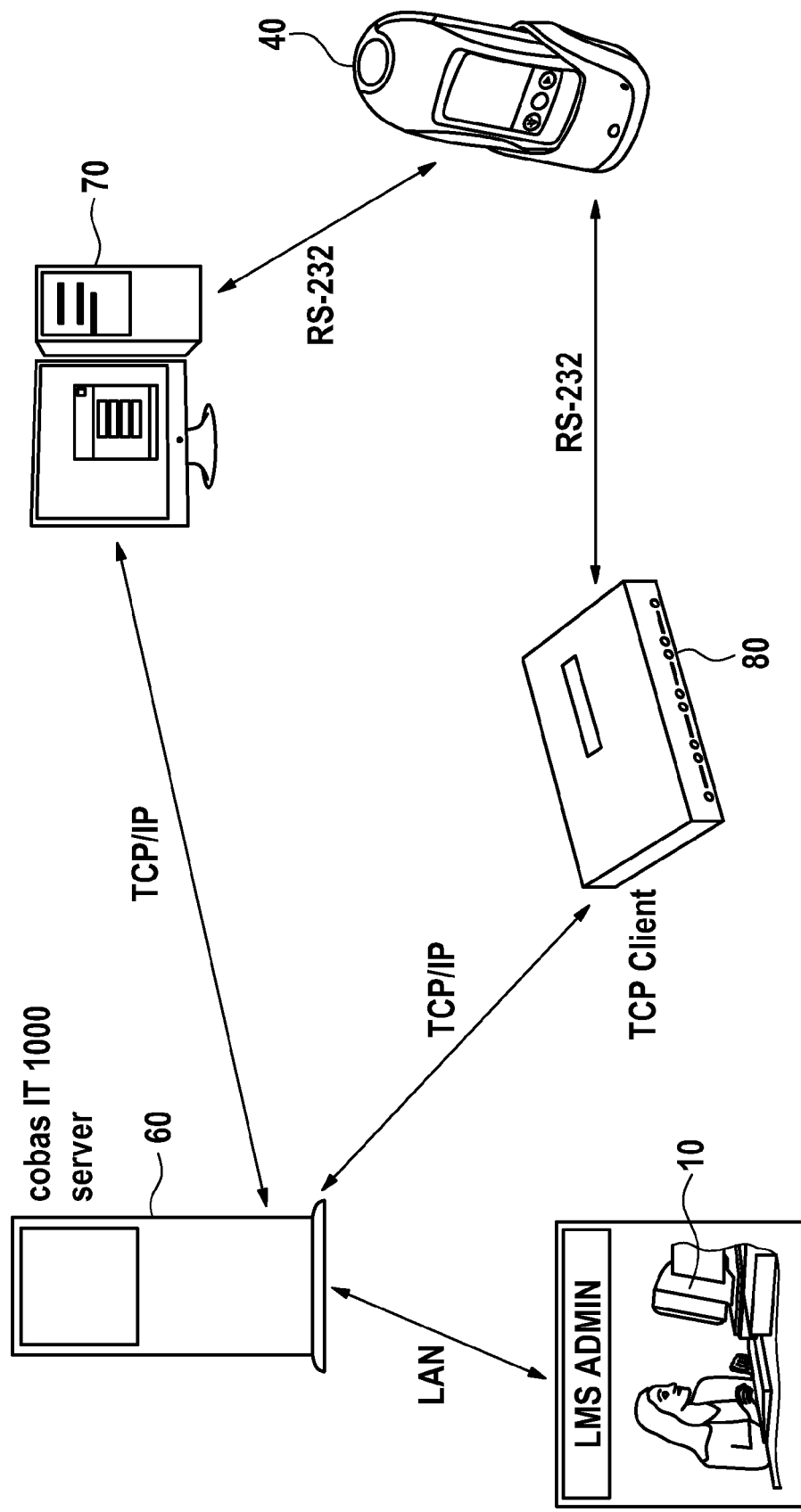
FIG. 5 depicts a connectivity scheme for conducting an embodiment of the present invention.

FIG. 5 shows a connectivity scheme of devices for embodying the present invention. The LMS administrator has a workstation 10 which is connected via a hospital network (typically a Local Area Network) to a cobas IT 1000 server 60 (i.e. a server running the cobas IT 1000 software). The cobas IT 1000 server 60 in this embodiment represents the Instrument Management System 30 according to the embodiment of the invention depicted in FIG. 1. The cobas IT 1000 server 60 is connected to a client computer 70 for sampling data from testing devices and to transmit the data to the cobas IT 1000 server 60. Further the analytical instrument or device 40 is connected via a modem 80 to the cobas IT 1000 server 60. An exam which is set up by the LMS administrator is downloaded to the cobas IT 1000 server 60 and can be taken by a user on the client computer 70 or on a terminal (e.g., terminal 20 in FIG. 1) connected to the client computer 70. The exam software or parts thereof may be installed on the cobas IT 1000 server 60 and the client computer 70. In a preferred embodiment the questions of the exam are transferred together to the client computer 70 and the answers are transmitted back to the cobas IT 1000 server 60 where they are evaluated. The result of the exam is then send to the client computer 70 to inform the user if he/she has passed the exam. The cobas IT 1000 server 60 updates the user list (i.e. a list of certified users) and transmits this via the client computer 70 or via the modem 80 to the analytical instrument(s) or device(s) 40.

Although not limited thereto, it is of an advantage that the IMS 30 (e.g., server 60) can be connected to a number of analytical instruments or device 40 so that the updated list of certified users can be send to them in parallel. This enables that certified users can do testing with not only one instrument but in principle with all of the instruments to which his/her certification is sent. These are e.g. all intensive care and bedside testing instruments located in the same hospital.

Persons skilled in the art will appreciate that the embodiments described herein may be subject to various improvements and/or modifications that may be apparent without departing from the spirit and scope of these embodiments.

What is claimed is:

1. A system for quality assured analytical testing, comprising:
   an Instrument Management System (IMS);
   an analytical instrument for conducting analytical testing, the analytical instrument having an input section for determining an actual user of the instrument and the analytical instrument being configured to run a testing routine; and a terminal connected to the Instrument Management System (IMS) which is remote from the analytical instrument and which provides an examination module of the IMS that is programmed to:

conduct an exam during which the examination module prompts questions to the user via the terminal which relate to the analytical instrument and/or a diagnostic test to be conducted therewith, receive via the terminal answers from the user to the questions, evaluate the answers, determine if the user has passed the exam, and transmit a user certificate to the analytical instrument if the user passed the exam, wherein the analytical instrument is programmed to check if a user certificate for the actual user is available and grant access to the testing routine by the user for conducting an analytical test only if a user certificate is available, wherein the IMS is configured to relay the user certificate to the analytical instrument, and wherein the IMS is a server.

2. The system of claim 1, wherein the analytical instrument communicates with the IMS and the IMS is configured to receive testing data from the analytical instrument.

3. The system of claim 1, wherein the user certificate comprises a user identification (ID) and optionally a user password.

4. The system of claim 1, wherein the analytical instrument is a handheld meter with an input section for inputting at least an user identification.

5. The system of claim 1, wherein analytical testing is performed extra corporally by reacting a patient sample with a reagent.

6. The system of claim 5, wherein said analytical testing is performed with a test element containing a reagent reacting with an analyte in the sample.

7. The system of claim 1, wherein the examination module is at least partially programmed by a supervisor to conduct an exam with questions specified by the supervisor.

8. A method for quality assured analytical testing, comprising:

prompting questions to a user which relate to an analytical test to be conducted or an analytical instrument to be employed, wherein the prompting questions and receiving answers are both conducted at a terminal connected to an Instrument Management System, and wherein the terminal provides an examination module of the Instrument Management System and is remote from the analytical instrument;

receiving the answers from the user to the questions;

evaluating the answers and determining, via the examination module, to which degree the answers are correct;

certifying the user, via the examination module, if the determined degree is above a preset threshold;

transmitting, via the examination module, a user certification to the analytical instrument;

prompting, via the analytical instrument, the user to input a user identification;

determining, via the analytical instrument, if the user is a certified user; and providing access to a testing routine of the analytical instrument if the user is a certified user, wherein the transmitting of the user certificate is via the Instrument Management System relaying the user certificate to the analytical instrument, and wherein the Instrument Management System is a server.

9. The method of claim 8 further comprising conducting an analytical test using the analytical instrument.

10. The method of claim 9 further comprising transmitting from the analytical instrument a result of the analytical test to the Instrument Management System.

11. The method according to claim 9, wherein said analytical testing is performed extra corporally by use of a test element which is used by the analytical instrument.

12. The system of claim 1, wherein the analytical instrument is programmed to check if a user certificate for the actual user is available by determining if the user is on a list of certified users.

13. The system according to claim 1, wherein the terminal is a client computer connected to the Instrument Management System.

14. The method according to claim 8, wherein determining, via the analytical instrument, if the user is a certified user is performed by determining if the user is on a list of certified users.

15. The method according to claim 8, further comprising directly connecting the analytical instrument to the terminal and then transmitting the user certificate to the analytical instrument.

16. The method according to claim 8, wherein the terminal is a workstation terminal.

* * * * *

UNITED STATES PATENT AND TRADEMARK OFFICE
CERTIFICATE OF CORRECTION

| | |
|---|---|
| PATENT NO. | : 8,495,707 B2 |
| APPLICATION NO. | : 12/543610 |
| DATED | : July 23, 2013 |
| INVENTOR(S) | : Miller |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 800 days.

Signed and Sealed this
Twenty-first Day of January, 2014

Michelle K. Lee
*Deputy Director of the United States Patent and Trademark Office*